United States Patent

Wacker

Patent Number: 5,382,675
Date of Patent: Jan. 17, 1995

[54] POLYCYCLIC COMPOUNDS AND PROCESSES FOR THE PREPARATION THEREOF

[75] Inventor: Oskar Wacker, Basel, Switzerland

[73] Assignee: Ciba-Geigy Corporation, Ardsley, N.Y.

[21] Appl. No.: 234,763

[22] Filed: Apr. 28, 1994

[30] Foreign Application Priority Data

May 7, 1993 [CH] Switzerland ............ 1406/93-6
Feb. 4, 1994 [CH] Switzerland ............ 335/94-0

[51] Int. Cl.$^6$ .................................. C07D 309/12
[52] U.S. Cl. .................................. 549/420; 540/545
[58] Field of Search ................................ 549/420

[56] References Cited

U.S. PATENT DOCUMENTS

| | | | |
|---|---|---|---|
| 4,100,177 | 7/1978 | Kelly | 549/420 |
| 4,100,178 | 7/1978 | Kelly | 549/420 |
| 4,304,924 | 12/1981 | Henrick et al. | 560/73 |
| 4,359,424 | 11/1982 | Henrick et al. | 549/416 |
| 5,043,335 | 8/1991 | Kleinschroth et al. | 540/545 |
| 5,093,330 | 3/1992 | Caravatti et al. | 514/211 |
| 5,185,260 | 2/1993 | Crisiman et al. | 540/545 |
| 5,264,431 | 11/1993 | Wacker et al. | 514/211 |

FOREIGN PATENT DOCUMENTS

| | | |
|---|---|---|
| 0383919 | 8/1990 | European Pat. Off. .. |
| 532178 | 3/1993 | European Pat. Off. . |
| 0575955 | 12/1993 | European Pat. Off. . |
| 9109034 | 6/1991 | WIPO . |

OTHER PUBLICATIONS

*copy provided by applicant.

Primary Examiner—C. Warren Ivy
Assistant Examiner—A. A. Owens
Attorney, Agent, or Firm—Irving M. Fishman; Karen G. Kaiser

[57] ABSTRACT

A tetrahydropyran-4-yloxy-alkanoic acid of formula III

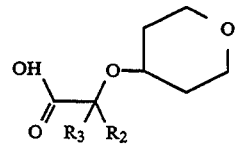

wherein $R_2$ is hydrogen or $C_{1-4}$ alkyl and $R_3$ is hydrogen or $C_{1-4}$ alkyl.

4 Claims, No Drawings

POLYCYCLIC COMPOUNDS AND PROCESSES FOR THE PREPARATION THEREOF

The invention relates to N-acylated staurosporin derivatives, namely N-(tetrahydropyran-4-yloxy-alkanoyl)-staurosporin derivatives, to processes and intermediates for the preparation thereof, to pharmaceutical compositions comprising those compounds, to the use thereof as medicaments and to processes for the preparation of the intermediates.

Staurosporin, the basic element of the derivatives according to the present invention was isolated already in the year 1977 from cultures of Streptomyces staurosporeus AWAYA, TAKAHASHI and OMURA, sp. nov. AM 2282, cf. S. Omura et al., J. Antibiot. 30, 275–281 (1977). Hitherto, only the relative, but not the absolute configuration of staurosporin was known. The absolute configuration was published only recently by N. Funato et al., Tetrahedron Letters 35:8, 1251–1254 (1994) and corresponds to the mirror image of the structure, used up to now in the literature to denote the relative configuration of staurosporine. Accordingly, in the Tetrahedron Letters publication it is literally recommended "that the stereochemical notation for staurosporin which has been in common use hitherto should be revised". Although the absolute configuration was not known hitherto, it was unequivocally fixed (defined) by the designation as "staurosporin derivatives". Therefore, in order to avoid errors upon comparison with the priority applications, the original formulae are still used in the present application.

Staurosporin exhibits a strong inhibitory activity on protein kinase C but also inhibits other protein kinases to an equally great extent and therefore does not have the selectivity required for therapeutic use. Although staurosporin derivatives substituted by customary acyl radicals, such as benzoyl, are more selective, those N-acylated staurosporin derivatives are generally comparatively poorly soluble and, therefore, cannot easily be formulated into suitable pharmaceutical dosage forms.

The aim of the present invention was to provide novel staurosporin derivatives that, whilst retaining the inhibitory activity of staurosporin on protein kinase C (PKC), especially on the "conventional" isotypes α, β-1, β-2 and γ of protein kinase C, principally on PKC-a and PKC-γ, are substantially less active in respect of other protein kinases and other isotypes of protein kinase C. In addition, the staurosporin derivatives to be provided should be highly active when administered orally and sufficiently soluble to be formulated into suitable pharmaceutical dosage forms without any great difficulty.

The invention relates especially to N-(tetrahydropyran-4-yloxy-alkanoyl)-staurosporin derivatives of formula I

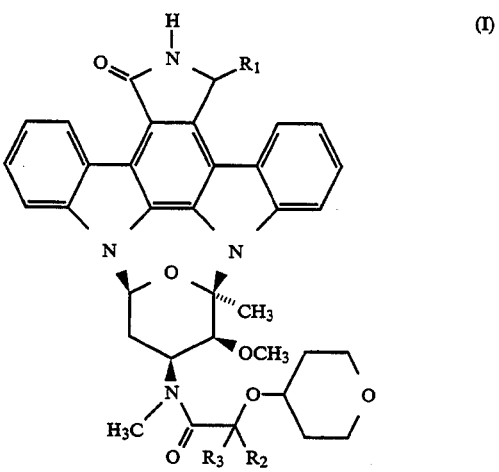

wherein
$R_1$ is hydrogen, hydroxy, lower alkoxy or oxo,
$R_2$ is hydrogen or $C_{1-4}$alkyl and
$R_3$ is $C_{1-4}$alkyl or preferably hydrogen,
to processes and intermediates for the preparation thereof, to pharmaceutical compositions comprising those compounds, to the use thereof as medicaments and to processes for the preparation of the intermediates.

The configurations evident from formula I are intended to designate only the relative, but not the absolute stereochemistry. As outlined above, the absolute stereochemistry is probably shown by the following formula Ia.

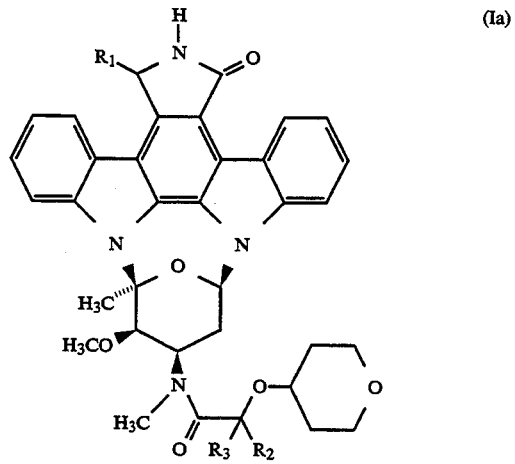

The configuration at the C—$R_2$ atom is (D) or (L), preferably (D).

Lower alkoxy $R_1$ is $C_1$-$C_7$alkoxy, preferably $C_{1-4}$ alkoxy, especially methoxy.

$C_{1-4}$alkyl $R_2$ or $R_3$ is preferably methyl.

The compounds of formula I exhibit valuable pharmacological properties: for example, they inhibit the enzyme protein kinase C with a high degree of selectivity. Phospholipid and calcium-dependent protein kinase C occurs in cells in several forms and participates in various fundamental processes, such as signal transmission, proliferation and differentiation, and also the release of hormones and neurotransmitters. The activation of that enzyme is effected either by receptor-mediated hydrolysis of phospholipids of the cell membrane or by direct interaction with certain tumour-promoting active substances. The sensitivity of the cell to receptor-mediated signal transmission can be substantially influenced by modifying the activity of protein kinase C (as a signal transmitter). Compounds that are capable of influencing the activity of protein kinase C can be used as tumour-inhibiting, anti-inflammatory, immunomodulating and antibacterial active ingredients and may even be of value as agents against atheroselerosis and disorders of the cardiovascular system and central nervous system.

Porcine brain protein kinase C purified in accordance with the procedure described by T. Uchida and C. R. Filburn in J. Biol. Chem. 259, 12311–4 (1984) is used to determine the inhibitory activity on protein kinase C. The inhibitory activity of the compounds of formula I on protein kinase C is determined in accordance with the procedure of D. Fabbro et al., Arch. Biochem. Biophys. 239, 102–111 (1985). In that test, the compounds of formula I inhibit protein kinase C at an $IC_{50}$ of as low as approximately from 0.01 to 0.05 $\mu$mol/liter. In contrast, the compounds of formula I inhibit other enzymes, for example protein kinase A and tyrosine protein kinase, only at a much greater concentration, for example a concentration 100 times greater, which demonstrates the selectivity of the compounds of formula I.

The porcine brain protein kinase C used in the above test is a mixture of various sub-types (isotypes) of protein kinase C. If pure recombinant isotypes are used in the above test instead of porcine brain protein kinase C it is found that the compounds of formula I inhibit the "conventional" isotypes $\alpha$, $\beta$-1, $\beta$-2 and $\gamma$ preferentially whereas the "non-conventional" isotypes $\delta$, $\epsilon$ and $\eta$ and the "atypical" isoform $\zeta$ are inhibited to a distinctly lesser extent and in some cases hardly at all.

Recombinant PKC isotypes are cloned, expressed and purified in the following manner: The production of various proteins with the aid of baculoviruses, and their cloning and isolation from Sf9 insect cells are carded out as described by M. D. Summers and G. E. Smith, "A manual method for baculovirus vectors and insect cell culture procedure", Texas Agricul. Exptl. Station Bull. (1987), 1555. The construction and isolation of recombinant viruses for the expression of PKC-$\alpha$ (bovine), PKC-$\beta$1 (human), PKC-$\beta$2 (human) and PKC-$\gamma$ (human/bovine hybrid) in Sf9 cells are effected in the manner described by Stabel et al. [S. Stabel, M. Liyanage and D. Frith, "Expression of protein kinase C isozymes in insect cells and isolation of recombinant proteins ", Meth. Neurosc. (1993)]. The production of the PKC isotypes in Sf9 cells is carded out in the manner indicated by Stabel et at. (see above), and the purification of the enzymes is effected in accordance with the method described in the publication by McGlynn et al. [E. McGlynn, J. Liebetanz, S. Reutener, J. Wood, N. B. Lydon, H. Hofstetter, M. Vanek, T. Meyer and D. Fabbro, "Expression and partial characterization of rat protein kinase C-$\delta$ and protein kinase C-$\gamma$ in insect cells using recombinant baculovirus", J. Cell. Biochem. 49, 239–250 (1992)]. For the generation of recombinant PKC-$\delta$ (rat), PKC-$\epsilon$ (rat), PKC-$\gamma$ (rat) and PKC-$\eta$ (mouse), and their expression and purification, the procedure described by Liyanage et al. ["Protein kinase C group B members PKC-$\delta$, -$\epsilon$, -$\zeta$ and PKC-$\lambda$: Comparison of properties of recombinant proteins in vitro and in vivo", Biochem. J. 283, 781–787 (1992)] and McGlynn et al., respectively, (see above) is followed, with the additional feature that the transfer vector pAc360 is used for the expression of PKC-$\eta$ [V. Luckow and M. D. Summers, "Trends in the development of baculovirus expression", Biotechnology 6, 47–55 (1988)].

The measurement of the activity of the recombinant PKC isotypes obtained by the above method is carded out in the absence of lipid and calcium (co-factors). Protamine sulfate phosphorylated in the absence of co-factors is used as the substrate. The activity of the enzymes reflects the transfer of $^{32}P$ from $\gamma$-[$^{32}P$]-ATP to protamine sulfate. Protamine sulfate is a mixture of polypeptides each comprising four C-terminal arginine residues. Phosphate incorporation is measured under the following conditions: 100 $\mu$l of the reaction mixture contain in final concentrations 20 mM TRIS-HCl pH 7.4, 10 mM Mg[$NO_3$]$_2$, 0.5 mg/ml of protamine sulfate, 10 $\mu$M ATP (0.1 $\mu$Ci $\gamma$-[$^{32}P$]-ATP; 10 Ci/mol; Amersham, Little Chalfont, United Kingdom), various concentrations of the inhibitory compounds and 0.5–2.5 U (units: a unit is the amount of enzyme that, in one minute and per milligram of protein, transfers one nanomole of $^{32}P$ from the above-mentioned $\gamma$-[$^{32}P$]-ATP to histone H1 [Sigma, type V-S]) of the enzymes. The reaction is started by the addition of the enzymes and transfer at 32° C. The reaction time is 20 minutes. The reaction is then stopped by dripping aliquots of 50 $\mu$l onto P81 chromatography paper (Whatman, Maidstone, United Kingdom). After removing unbound $\gamma$-[$^{32}P$]-ATP and nucleotide fragments by washing operations as described by J. J. Witt and R. Roskoski, "Rapid protein kinase assay using phospho-cellulose-paper absorption", Anal. Biochem. 66, 253–258 (1975), the substrate phosphorylation is determined by scintillation measurement. In that test, the compounds of formula I inhibit the various isotypes of protein kinase C (PKC) at an $IC_{50}$ of as low as approximately from 0.001 to 0.1 $\mu$mol/liter in the case of PKC-$\alpha$ and PKC-$\gamma$, approximately from 0.01 to 0.08 $\mu$mol/liter in the case of PKC-$\beta$-1 and PKC-$\beta$-2, approximately from 0.03 to 10 $\mu$mol/liter in the case of PKC-$\delta$, PKC-$\epsilon$ and PKC-$\eta$, and more than 4 $\mu$mol/liter in the case of PKC-$\zeta$.

As may be expected purely on the basis of the above-described inhibitory activity on protein kinase C, the compounds of formula I exhibit antiproliferative properties which can be demonstrated directly in another test described in the following in which the inhibitory activity of the compounds of formula I on the growth of human T24 bladder carcinoma cells is determined. Those cells are incubated in Eagle's minimal essential medium, to which 5 % (v/v) foetat calf serum has been added, in a humidified incubator at 37° C. and with 5 % by volume of $CO_2$ in the air. The carcinoma cells (1000–1500) are sown in 96-well microtitre plates and incubated overnight under the above-mentioned conditions. The test compound is added in serial dilutions on day 1. The plates are incubated for 5 days under the above-mentioned conditions. During that period the control cultures undergo at least four cell divisions. After incubation, the cells are fixed with 3.3 % (w/v) aqueous glutaraldehyde solution, washed with water and stained with 0.05 % (weight/volume) aqueous methylene blue solution. After washing, the dye is eluted with 3 % (w/v) aqueous hydrochloric acid. The optical density (OD) per well, which is directly proportional to the number of cells, is measured at 665 nm using a photometer (Titcrick multiskan). The $IC_{50}$ values are calculated with a computer system using the formula $$\frac{OD_{665} \text{ (test) minus } OD_{665} \text{ (start)}}{OD_{665} \text{ (control) minus } OD_{665} \text{ (start)}} \times 100.$$

The $IC_{50}$ values are defined as being the concentration of active ingredient at which the number of cells per well is only 50 % of the number of cells in the control cultures at the end of the incubation period. In the case of the compounds of formula I, the $IC_{50}$ values so obtained are approximately from 0.01 to 0.9 μmol/liter, especially approximately from 0.03 to 0.9 μmol/liter.

The anti-tumour activity of the compounds of formula I can also be demonstrated in vivo:

Female Balb/c hairless mice with s.c. transplanted human bladder tumours 724 are used to determine the anti-tumour activity. With the animals under peroral forene narcosis, approximately 25 mg of a solid tumour are placed under the skin on the animals' left flank on day 0 and the small incised wound is closed by means of suture clips. On day 6 after the transplantation, the mice are divided at random into groups of 6 animals and treatment commences. The treatment is carded out for 15 days with peroral or intraperitoneal administration once daily of a compound of formula I in dimethyl sulfoxide/Tween 80/sodium chloride solution in the various doses. The rumours are measured twice a week with a slide gauge and the volume of the tumours is calculated. In this test, the peroral or intraperitoneal administration of 3 mg/kg daily of a compound of formula I brings about a reduction in the average tumour volume to from 10 to 15% of the tumour volume in the untreated control animals.

On the basis of the properties described, the compounds of formula I can be used especially as tumour-inhibiting active ingredients, for example in the treatment of tumours of the bladder and the skin. When the compounds of formula I are used in the treatment of cancer in combination with other chemotherapeutic agents, they prevent the development of resistance (multidrug resistance) or eliminate an already existing resistance to the other chemotherapeutic agents. They are also suitable for the other uses mentioned above for protein kinase C modulators and can be used especially in the treatment of disorders responsive to inhibition of protein kinase C.

The compounds of formula I also inhibit certain tyrosine kinases, such as, especially, PDGF receptor kinase, even at an $IC_{50}$ of less than 0.08 μmol/liter.

PDGF (Platelet-derived Growth Factor) is a very frequently occurring growth factor which plays an important part both in normal growth and in pathological cell proliferation, such as in carcinogenesis and disorders of the smooth muscle cells of blood vessels, for example in atherosclerosis and thrombosis.

The inhibition of protein kinase C and PDGF receptor kinase acts in that respect quasi synergistically in the same way with a view to regulating cell growth.

The inhibition of PDGF-stimulated receptor tyrosine kinase activity in vitro is measured in PDGF receptor immune complexes of Balb/c 3T3 cells in a manner analogous to that described by E. Andrejauskas-Buchdunger and U. Regenass in Cancer Research 52, 5353-5358 (1992). The compounds of formula I described in more detail above inhibit PDGF-dependent cell-free receptor phosphorylation at concentrations of less than 0.08 μmol/liter.

The inhibition of PDGF receptor tyrosine kinase in the intact cell is demonstrated by Western blot analysis, likewise in a manner analogous to that described by E. Andrejauskas-Buchdunger and U. Regenass in Cancer Research 52, 5353-5358 (1992). In that test the inhibition of the ligand-stimulated PDGF receptor autophosphorylation in Balb/c murine cells is measured by means of anti-phosphotyrosine antibodies. The compounds of formula I inhibit the tyrosine kinase activity of the PDGF receptor at concentrations of from 0.005 to 0.08 μmol/liter. Those compounds also inhibit the cell growth of a PDGF-dependent cell line, namely BALB/c 3T3 murine fibroblasts, at concentrations of less than 1.0 μmol/liter.

On the basis of the properties described, the compounds of formula I can be used not only as tumour-inhibiting active ingredients but also as agents against non-malignant proliferatire disorders, such as atherosclerosis, thrombosis, psoriasis, sclerodermia and fibrosis. They are also suitable for the other uses mentioned above for protein kinase C molulators and can be used especially in the treatment of disorders responsive to inhibition of PDGF receptor kinase.

Compounds of formula I wherein $R_1$ is hydrogen or oxo, $R_2$ is hydrogen or $C_{1-4}$alkyl and $R_3$ is hydrogen are preferred.

Compounds of formula I wherein $R_1$ is hydrogen or oxo, $R_2$ is hydrogen or methyl and $R_3$ is hydrogen are especially preferred.

The above-mentioned compounds of formula I that have the (D)-configuration at the C-$R_2$ atom are more especially preferred.

The compounds of formula I described in the Examples, especially N-[O-(tetrahydropyran-4-yl)-D-lactoyl]-staurosporin, are even more especially preferred.

The compounds of formula I are prepared in accordance with processes known per se. The process according to the invention comprises acylating an amine of formula II

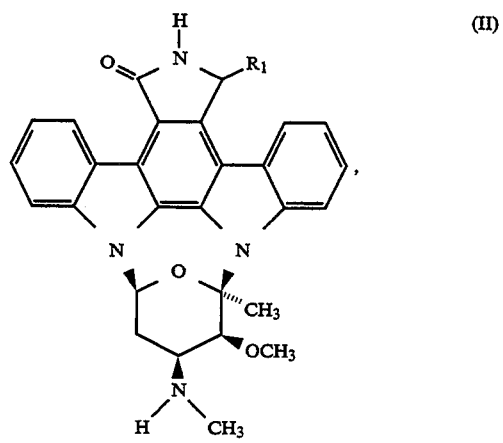

wherein $R_1$ is as defined above with the proviso that a hydroxy group represented by $R_1$ is if necessary protected by a readily removable hydroxy-protecting group, with a carboxylic acid of formula IH

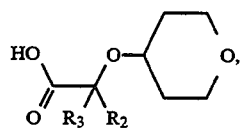

(III)

wherein $R_2$ and $R_3$ are as defined above, or with a reactive carboxylic acid derivative thereof, and removing protecting groups, which are not present in the desired end product of formula I, and, if desired, separating a resulting mixture of isomers.

The manner in which the above-mentioned process is carded out is explained in more detail hereinafter: protecting groups and the manner in which they are introduced and removed are described, for example, in "Protective Groups in Organic Chemistry", Plenum Press, London, New York 1973, and in "Methoden der organischen Chemic", Houben-Weyl, 4th edition, Vol. 15/1, Georg-Thieme-Verlag, Stuttgart 1974 and in Theodors W. Greene, "Protective Groups in Organic Synthesis", John Wiley & Sons, New York 1981. A characteristic of protecting groups is that they can be readily removed, that is to say, without undesired secondary reactions taking place, for example by solvolysis, reduction, photolysis or also under physiological conditions.

Hydroxy-protecting groups are, for example, acyl radicals, such as unsubstituted or substituted, for example halogen-substituted, lower alkanoyl, such as 2,2-dichloroacetyl, or acyl radicals of carbonic acid semiesters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, and also trityl or formyl, or organic silyl or stannyl radicals, and also readily removable etherifying groups, such as tert-lower alkyl, for example tert-butyl, 2-oxa- or 2-thiaaliphatic or-cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5 or 6 ring atoms, for example tetrahydrofuryl or 2-tetrahydropyranyl or corresponding this analogues, and also unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

The removal of the protecting groups, which are not constituents of the desired end product of formula I, is carded out in a manner known per se, for example by solvolysis, especially hydrolysis, alcoholysis or acidolysis, or by reduction, especially hydrogenolysis or chemical reduction. Hydroxy protected by unsubstituted or substituted 1-phenyl-lower alkyl, for example benzyl, is freed preferably by catalytic hydrogenation, for example in the presence of a palladium-on-carbon catalyst. A hydroxy group protected by 2,2-dichloroacetyl is freed, for example, by basic hydrolysis, and a hydroxy group etherified by tert-lower alkyl or by a 2-oxa- or 2-thia-aliphatic or-cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed by a hydrofluoric acid salt yielding fluoride anions, for example tetrabutylammonium fluoride.

A reactive acid derivative of a compound of formula III is especially a reactive (activated) ester, a reactive anhydride or a reactive cyclic amide.

Reactive (activated) esters of an acid of formula III are especially esters unsaturated at the linking carbon atom of the esterifying radical, especially of the vinyl ester type, such as vinyl esters themselves (which can be obtained, for example, by transesterifying a corresponding ester with vinyl acetate; activated vinyl ester method), carbamoyl vinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-di-substituted amidino esters (which can be obtained, for example, by treating the corresponding acid with a suitable N,N'-di-substituted carbodiimide, for example N,N'-dicyclohexylcarbodiimide or N-ethyl-N'-(3-dimethylaminopropyl)-carbodiimide hydrochloride; carbodiimide method), or N,N-di-substituted amidino esters (which can be obtained, for example, by treating the corresponding acid with an N,N-di-substituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (which can be obtained, for example, by treating the corresponding acid with chloroacetonitrile in the presence of a base; cyanomethyl esters method), thio esters, especially unsubstituted or substituted, for example nitro-substituted, phenylthio esters (which can be obtained, for example, by treating the corresponding acid with unsubstituted or substituted, for example nitro-substituted, thiophenols, inter alia by the anhydride or carbodiimide method; activated thiol esters method), amino or amido esters (which can be obtained, for example, by treating the corresponding acid with an N-hydroxy-amino or N-hydroxy-amido compound, for example N-hydroxy-succinimide, N-hydroxy-piperidine, N-hydroxy-phthalimide or 1-hydroxy-benzotriazole, for example by the anhydride or carbodiimide method; activated N-hydroxy esters method) or silyl esters (which can be obtained, for example, by wearing the corresponding acid with a silylating agent, for example hexamethyldisilazane, and which react readily with hydroxy groups but not with amino groups).

Anhydrides of an acid of formula HI may be symmetric or preferably mixed anhydrides of those acids, for example anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and treatment thereof with nitrous acid; azide method), anhydrides with carbonic acid semi-derivatives, such as with corresponding esters, for example carbonic acid lower alkyl semiesters (which can be obtained, for example, by treating the corresponding acid with haloformic acid lower alkyl esters, such as chloroformic acid lower alkyl esters, or with a 1-lower alkoxycarbonyl-2-lower alkoxy-1,2-dihydroquinoline, for example 1-lower alkoxycarbonyl-2-ethoxy-1,2-dihydroquinoline; mixed 0-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (which can be obtained, for example, by treating a salt, such as an alkali metal salt, of the corresponding acid with a suitable organic sulfonic acid halide, such as a lower alkane- or aryl-sulfonic acid chloride, for example methane- or p-toluene-sulfonic acid chloride; mixed sulfonic acid anhydrides method) and symmetric anhydrides (which can be obtained, for example, by condensing the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

Derivatives of acids of formula III that are used as acylating agents can also be formed in situ. For example, N,N'-di-substituted amidino esters can be formed in situ by reacting a mixture of the starting material of formula V and the acid used as acylating agent in the presence of a suitable N,N-di-substituted carbodiimide, for example N,N'-dicyclohexylcarbodiimide. In addition, amino or amido esters of the acids used as acylating agents can be formed in the presence of the starting material of formula V to be acylated, by reacting a mixture of the corresponding acid and amino starting materials in the presence of an N,N'-di-substituted carbodiimide, for example N,N'-dicyclohexylcarbodiimide, and of an N-hydroxy-amine or N-hydroxy-amide, for example N-hydroxysuccinimide, where appropriate in the presence of a suitable base, for example 4-dimethylaminopyridine.

The reaction can be carded out in a manner known per se, the reaction conditions depending especially upon whether and how the carboxy group of the acylating agent of formula III has been activated, generally in the presence of a suitable solvent or diluent or a mixture thereof, and, if necessary, in the presence of a condensation agent which, for example when the carboxy group participating in the reaction is in the form of an anhydride, may also be an acid-binding agent, with cooling or heating, for example in a temperature range of from approximately −30° C. to approximately +150° C., especially approximately from 0° C. to +100° C., preferably from room temperature (approximately 20° C.) to +70° C., in an open or closed reaction vessel and/or in the atmosphere of an inert gas, for example nitrogen. Customary condensation agents are, for example, carbodiimides, for example N,N'-diethyl-, N,N'-dipropyl- or N,N'-dicyclohexyl-carbodiimide, suitable carbonyl compounds, for example carbonyldiimidazole, or 1,2-oxazolium compounds, for example 2-ethyl-5-phenyl-1,2-oxazolium-3 '-sulfonate and 2-tert-butyl-5-methyl-isoxazolium perchlorate, or a suitable acylamino compound, for example 2-ethoxy-1-ethoxycarbonyl-1,2-dihydroquinoline. Water-soluble carbodiimides, such as N-ethyl-N'-(3-dimethylaminopropyl)-carbodiimide, are advantageous. Customary acid-binding condensation agents are, for example, alkali metal carbonates or hydrogen carbonates, for example sodium or potassium carbonate or hydrogen carbonate (customarily together with a sulfate), or organic bases, such as customarily sterically hindered tri-lower alkylamines, for example N,N-diisopropyl-N-ethylamine.

Mixtures of isomers can be separated into the individual isomers in a manner known per se, for example by fractional crystallisation, chromatography etc.

The starting materials of formula II are known or can be prepared in accordance with processes known per se. The starting material of formula II wherein $R_1$ is hydrogen, that is to say, staurosporin, is commercially available and can be prepared by fermentation with the strain Streptomyces staurosporeus. That strain was deposited under number FERM P-3725 at the Fermentation Research Institute, Japan, in connection with the examined Japanese patent publication, Kokoku, No. 57–53 076 which was published on Nov. 11, 1982, see S. Omura et at., J. Antibiot. 30, 275–281 (1977). Staurosporin derivatives of formula II wherein $R_1$ is other than hydrogen are described, for example, by I. Takahashi et al., J. Pharmacol. Exp. Ther. 255(3) (1990) 1218–1221 and in WO-A-8907-105-A (Applicant: Kyowa Hakko Kogyo KK, Japanese priority No. 024 571 of Apr. 2, 1988). Compounds of formula I wherein $R_1$ is hydroxy or oxo are also obtained as secondary products in the synthesis of compounds of formula I wherein $R_1$ is hydrogen.

The starting materials of formula III are novel. An acid of formula III is obtained by reacting tetrahydropyran-4-ol with an acid of formula IV

wherein X is a nucleophilic leaving group and $R_2$ and $R_3$ are as defined above. A nucleophilic leaving group X is especially hydroxy esterified by a suitable mineral acid, such as a suitable hydrohalic acid, or a suitable sulfonic acid, such as 4-toluenesulfonic acid, preferably chlorine. Tetrahydropyran-4-ol is first reacted in a suitable inert aprotic solvent, such as an acyclic or cyclic ether, such as dioxane, with a suitable base, such as sodium hydride. The resulting suspension is added dropwise to a solution of a compound of formula IV in a suitable inert aprotic solvent, such as an acyclic or cyclic ether, such as dioxane. The reaction is carded out at from 0° C. to 150° C., preferably from 20° C. to 100° C., for example at the reflux temperature of the solvent used.

The invention relates also to the novel compounds of formula III and their salts as intermediates for the preparation of the compounds of formula I. The compounds of formula III are surprisingly soluble in water and organic solvents. The water solubility at 22° C. is from 100 g to 500 g/liter. It is therefore possible that the corresponding acyl radicals of the compounds of formula III are largely responsible for the substantially increased solubility, for example increased more than 10-fold, of the compounds of formula I in water and other solvents, by comparison with that of other N-acyl-staurosporin derivatives, such as N-benzoyl-staurosporin.

Preferred are compounds of formula III wherein $R_2$ is hydrogen or methyl and $R_3$ is hydrogen or methyl, especially the compounds of formula III described in the Examples and the salts thereof.

Salts of compounds of formula III are especially metal or ammonium salts, such as alkali metal or alkaline earth metal salts, for example sodium, potassium, magnesium or calcium salts, or ammonium salts with ammonia or with suitable organic amines, such as tertiary monoamines, for example triethylamine or tri-(2-hydroxyethyl)-amine, or heterocyclic bases, for example N-ethyl-pipefidine or N,N'-dimethyl-piperazine.

The invention relates also to the process described above for the preparation of the novel compounds of formula III.

The processes described above, including the processes for removing protecting groups and the additional process measures are, unless otherwise indicated, carded out in a manner known per se, for example in the presence or absence of preferably inert solvents or diluents, if necessary in the presence of condensation agents or catalysts, at reduced or elevated temperature, for example in a temperature range of from approximately $-20°$ C. to approximately $150°$ C., especially from approximately $0°$ C. to approximately $+70°$ C., preferably from approximately $+10°$ C. to approximately $+50°$ C., principally at room temperature, in a suitable vessel and, if necessary, in an inert gas atmosphere, for example a nitrogen atmosphere.

Taking into account all the substituents in the molecule, if necessary, for example if readily hydrolysable radicals are present, especially mild reaction conditions are to be used, such as short reaction times, the use of mild acidic or basic agents in low concentration, stoichiometric ratios, and the selection of suitable catalysts, solvents, temperature conditions and/or pressure conditions. The invention relates also to the use of the compounds of formula I, preferably in the form of pharmaceutical compositions, in the therapeutic treatment of the human or animal body, especially in the case of the above-mentioned disorders. The invention relates also to a method of inhibiting protein kinase C in a warm-blooded animal requiring such treatment, which comprises administering to that warm-blooded animal a dose that is effective in inhibiting protein kinase C of a compound of formula I. The dose of the active ingredient depends, inter alia, on the nature of the disorder, the type and size of the species to be treated, the organism's resistance and the mode of administration. For example, a warm-blooded animal of approximately 70 kg body weight receives a daily dose of from 1 mg to 1500 mg, principally from 100 mg to 1000 mg, preferably from 200 mg to 800 mg, for example 500 mg, of a compound of formula I. That total daily dose is preferably divided into 2 or 3 administrations daily. The dose for oral administration is approximately from two to three times greater than for parenteral administration, that is to say, it tends towards the upper range of the doses indicated.

The invention relates also to pharmaceutical compositions comprising an effective amount, especially an amount effective in the prophylaxis or treatment of one of the above-mentioned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets may also comprise binders, for example magnesium aluminium silicate, starches, such as corn, wheat or flee starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. It is also possible to use the pharmacologically active compounds of the present invention in the form of parenterally administrable compositions or in the form of infusion solutions. Such solutions are preferably isotonic aqueous solutions or suspensions which, for example in the case of lyophilised compositions that comprise the active ingredient alone or together with a carrier, for example mannitol, can be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances, such as antibiotics, are prepared in a manner known per se, for example by means of conventional mixing, granulating, confectioning, dissolving or lyophilising processes, and comprise approximately from 0.01% to 90%, in the case of lyophilisates up to 100%, especially from approximately 0.1% to approximately 50%, especially from 1% to 30%, of the active ingredient(s), an active ingredient concentration of less than 1% being suitable especially for compositions that are to be applied topically.

The following Examples illustrate the invention without limiting it in any way. The $R_f$ values are determined on silica gel thin-layer plates (Merck, Darmstadt, Germany). The ratio of the eluants in the eluant mixtures used is indicated in pans by volume (v/v) and temperatures are indicated in degrees Celsius. The concentration, c, of the compound in the solvent or solvent mixture is, in the case of the optical rotation, indicated as a percentage (weight/volume).

EXAMPLE 1

At 0°, 1.17 g (7.8 mmol) of 1-hydroxybenzotriazole and 1.61 g (7.8 mmol) of N,N'-dicyclohexylcarbodiimide are added to a solution of 1.13 g (6.5 mmol) of 0-tetrahydropyran-4-yl-D-lactic acid in 75 ml of absolute N,N'-dimethylformamide and the resulting clear colourless solution is stirred for 3 hours at 0°. 2.33 g (5.01 mmol) of staurospofin are then added and the resulting colourless suspension is stirred for 1 hour at 0° and for 20 hours at room temperature. Then, in order to ensure that the staurosporin used has been completely reacted, an active ester solution of 0.38 g (2.18 mmol) of 0-tetrahydropyran-4-yl-D-lactic acid, 0.39 g (2.60 mmol) of 1-hydroxybenzotriazole and 0.54 g (2.60 mmol) of N,N'-dicyclohexylcarbodiimide in a total of 25 ml of absolute N,N'-dimethylformamide is added again and the batch is stirred for one hour at 0° and then for a further 18 hours at room temperature. The resulting yellowish suspension is poured into 300 ml of water and stirred for one hour at room temperature and the precipitated crystals are filtered off with suction and washed with water. The aqueous phase is discarded. The filter material is suspended in 130 ml of methylene chloride and stirred for 1.5 hours at room temperature. The precipitated N,N'-dicyclohexylurea is filtered off with suction and washed with methylene chloride and the filtrate is concentrated to dryness by evaporation under a high vacuum at 30°. The residue (yellow crystals) is purified by column chromatography on 300 g of silica gel (type Si60, Merck 9385, 0.040–0.063 mm) in chloroform (25 ml fractions). Fractions 220–305 are combined and concentrated to dryness by evaporation under a high vacuum at 30°. The residue (yellow crystals) is recrystallised twice from ethyl acetate to give N-[O-(tetrahydropyran-4-yl)-D-lactoyl]-staurosporin in the form of slightly yellowish crystals of m.p. 222°–223° (sintering from 220°) which still contain 0.19 mol of water, $[\alpha]_D^{20} = +166.9 \pm 2.0°$ (c=0.498; methanol).

The starting material is obtained as follows:

Stage 1.1

4.8 g (120 mmol) of 60% sodium hydride in oil (Fluka, pract.) are added at 65° to a solution of 3.06 g (2.85 ml, d=1.074; 29.96 mmol) of tetrahydro-2H-pyran-4-ol (Fluka, pract.) in 100 ml of absolute 1,4-dioxane. The resulting grey suspension is stirred under reflux for 2 hours, is allowed to cool to 65° again and then a solution of 3.25 g (2.59 ml, d=1.25; 29.95 mmol) of S(−)-2-chloropropionic acid (Fluka, puriss.) in 60 ml of absolute 1,4-dioxane is added dropwise over a period of 8 minutes. The resulting brown suspension is diluted with 100 ml of absolute 1,4-dioxane and the batch is heated under reflux for 3 hours, with stirring. Stirring is then continued for a further 14 hours at room temperature. 40 ml of water are then added dropwise to the resulting brown suspension over a period of 2 minutes and the yellow solution obtained is concentrated to dryness by evaporation under a high vacuum. The residue is taken up in 200 ml of water and the aqueous solution is extracted once with 250 ml and once with 150 ml of ethyl acetate. The ethyl acetate extracts are then washed once with 100 ml of water. All the aqueous phases are combined and then acidified with 4N hydrochloric acid (pH 1). The resulting solution is saturated with sodium chloride and extracted twice with 300 ml of ethyl acetate each time. The organic phases are then washed three times with 150 ml of saturated sodium chloride solution each time. All the ethyl acetate extracts are then combined, dried over magnesium sulfate, filtered and concentrated to dryness by evaporation under a high vacuum at 30°. The residue (yellow oil) is purified by bulb tube distillation (b.p. approximately 160° at 0.6 mm Hg). O-(tetrahydropyran-4-yl)-D-lactic acid is obtained in the form of a slightly yellowish oil; $[\alpha]_D^{20} = +46.7 \pm 0.9°$ (c=1.058; chloroform). The oil crystallises from ethyl acetate/hexane 1:1 in the form of colourless crystals having a melting point of 68.7°–69.5°; $[\alpha]_D^{20} = +48.8 \pm 0.8°$ (c=1; chloroform)

EXAMPLE 2

From the mother liquors of the recrystallisations of the end product of Example 1. there is isolated by flash chromatography at 0.4 bar on 90 g of silica gel (type Si60, Merck 9385, 0.040–0.063 mm) in methylene chloride/methanol (98:2; 10 ml fractions), after concentrating fractions 23–27 to dryness by evaporation under a high vacuum, N-[O-(tetrahydropyran-4-yl)-D-lactoyl]-7-oxo-staurospofin in the form of yellow crystals of m.p. 206°–208° (without recrystallisation), (+)FAB, MS: (M+H)+=637, $[\alpha]_D^{20} = +138.7 \pm 10.8°$ (c=0.185; methanol:chloroform=1:1).

EXAMPLE 3

9.16 g (61.0 mmol) of 1-hydroxybenzotriazole and 11.7 g (61.0 mmol) of N-ethyl-N'-(3-dimethylaminopropyl)-carbodiimide hydrochloride (EDC) are added at 0° under argon to a solution of 8.16 g (46.9 mmol) of 0-tetrahydropyran-4-yl-D-lactic acid in 400 ml of absolute N,N'-dimethylformamide and the resulting clear colourless solution is stirred for 3 hours at 0°. 17.50 g (37.5 mmol) of staurosporin are then added and the resulting yellowish solution is stirred for 2 hours at 0° and for 19 hours at room temperature. The yellowish solution is subsequently concentrated to dryness by evaporation under a high vacuum. The residue is stirred for 15 minutes with 250 ml of water, the batch is filtered with suction and the resulting beige crystals are washed with water. The crystals are purified by flash chromatography at 0.4 bar on 500 g of silica gel (type Si60, Merck 9385, 0.040–0.063 mm) in methylene chloride/methanol (98:2; 25 ml fractions). Fractions 70–140 are combined and concentrated by evaporation under a high vacuum at 30°. The residue is crystallised from 400 ml of ethyl acetate, and N-[O-(tetrahydropyran-4-yl)-D-lactoyl]-staurospofin that is almost pure according to thin-layer chromatography is obtained in the form of beige crystals. Fractions 45–69 and 141–170 of the above-mentioned flash chromatography are likewise combined and concentrated by evaporation under a high vacuum. The yellow crystals so obtained and the yellow crystals from the mother liquor of the first recrystallisation are subjected to flash chromatography again on 500 g of silica gel Si60 under the same conditions as those already described. After concentrating by evaporation the TLC-pure fractions of the second flash chromatography operation, the products are combined with the beige crystals first obtained and recrystallised again from 800 ml of ethyl acetate to give N-[O-(tetrahydropyran-4-yl)-D-lactoyl]staurospofin in the form of beige crystals of m.p. 220°–222° (sintering from 214°) which still contain 0.42 mol of water; $[\alpha]_D^{20} = +166.6 \pm 2.5°$ (c=0.404; methanol).

EXAMPLE 4

Analogously to Example 3, there is obtained from 310 mg (1.78 mmol) of O-tetrahydropyran-4-yl-L-lactic acid, 347 mg (2.31 mmol) of 1-hydroxybenzotriazole, 443 mg (2.31 mmol) of N-ethyl-N'-3-(3-dimethylaminopropyl)-carbodiimide hydrochloride (EDC) and 664 mg( 1.42 mmol) of staurosporin in 15 ml of absolute N,N'-dimethylformamide, after a reaction time of 5 hours at 0° and 16 hours at room temperature under argon and subsequent analogous flash chromatography, N-[O-(tetrahydropyran-4-yl)-L-lactoyl]-staurospofin in the form of beige crystals of m.p. 302°–304° (sintering from 280°; from ethyl acetate); $[\alpha]_D^{20} = +145.6 \pm 1.8°$ (C=0.544; chloroform).

The starting material is obtained as follows:
Stage 4.1

Analogously to stage 1.1, there is obtained from 1.021 g (0.951 ml, d=1.074; 10 mmol) of tetrahydro-2H-pyran-4-ol (Fluka, pract.), 1.60 g of sodium hydride (60% strength in oil, Fluka pract.) and 1.08 g (0.863 ml, d=1,258; 10 mmol) of R(+)-2-chloropropionic acid (Fluka, puriss.) in a total of 55 ml of 1,4-dioxane, after concentration of the ethyl acetate extracts by evaporation and after bulb tube distillation of the resulting residue (b.p. approximately 160°, at 0.8 mm Hg), 0-(tetmhydropyran-4-yl)-L-lactic acid in the form of a colourless oil which, on being left to stand, solidifies to colourless crystals which melt at from 33.7 to 67.6° and still contain 0.13 mol (1.30%) of water; $[\alpha]_D^{20} = -46.7 \pm 1.0°$ (c=1.035; chloroform).

EXAMPLE 5

Analogously to Example 3 there is obtained from 200 mg (1.25 mmol) of O-tetrahydropyran-4-yl-glycolic acid, 244 mg (1.62 mmol) of 1-hydroxybenzotriazole, 311 mg (1.62 mmol) of N-ethyl-N'-(3-dimethylaminopropyl)-carbodiimide hydrochloride (EDC) and 466 mg (1.0 mmol) of staurosporin in 10 ml of absolute N,N'-dimethylformamide, after a reaction time of 2 hours at 0° and 18 hours at room temperature, flash chromatography (analogously to Example 3, but 20 ml fractions, product in fractions 15-20) and recrystallisation of the product so purified from ethyl acetate/hexane (1:1), N-[2-(tetrahydropyran-4-yloxy)-acetyl]-staurosporin in the form of beige crystals of m.p. 222°-224° (sintering from 215°) which still contain 0.29 mol of water; $[\alpha]_D^{20} = +180.0 \pm 2.0°$ (c=0.510; chloroform), $R_f=0.26$ (methylene chloride:ethanol=95:5); $R_f=0.48$ (acetone); $R_f=0.64$ (methylene chloride:methanol=9:1).

The starting material is obtained as follows:
Stage 5.1

At 65°, 3.20 g (80 mmol) of 60% sodium hydride in oil (Fluka, pract.) are added to a solution of 2.042 g (1.902 ml, d=1.074; 20.0 mmol) of tetrahydro-2H-pyran-4-ol (Fluka, pract.) in 70 ml of absolute 1,4-dioxane. The resulting grey suspension is stirred for 3 hours under reflux, is allowed to cool to 65° again and then a solution of 1.89 g (20.0 mmol) of chloroacetic acid (Fluka, puriss.) in 40 ml of absolute 1,4-dioxane is added dropwise over a period of 20 minutes. The resulting grey-brown suspension is then heated to reflux again and stirred for 3 hours at that temperature. After stirring for a further 16 hours at room temperature, 10 ml of water are added dropwise over a period of 5 minutes and the resulting yellowish suspension is concentrated to dryness by evaporation under a high vacuum. The residue is taken up in 20 ml of water and the aqueous solution is extracted twice with 20 ml of ethyl acetate each time. The ethyl acetate extracts are then washed once with 10 ml of water. The aqueous phases are combined and then acidified with 4N hydrochloric acid (pH 1). The resulting solution is saturated with sodium chloride and extracted twice with 50 ml of ethyl acetate each time. The ethyl acetate phases are then washed twice with 20 ml of saturated sodium chloride solution each time. All the ethyl acetate extracts are subsequently combined, dried over magnesium sulfate, filtered and concentrated to dryness by evaporation under a high vacuum at 30°. The residue (yellow oil) is purified by bulb tube distillation (b.p. approximately 130° at 0.4 mm Hg) to give O-(tetrahydropyran-4-yl)-glycolic acid in the form of a colourless oil which, on being left to stand, solidifies to colourless crystals which melt at from 63.9° to 70.6° (sintering from 60.2°) and contain 0.08 mol (0.91%) of water.

EXAMPLE 6

From fractions 9-11 of the flash chromatography of Example 5 there is obtained as a secondary product, after recrystallisation from ethyl acetate/hexane 1:1, N-[2-(tetrahydropyran-4-yloxy)-acetyl]-7-oxo-staurosporin in the form of yellow crystals of melting point 190.7°-192.4° (sintering from 187°) which still contain 0.35 mol of water; $[\alpha]_D^{20} = +157.4 \pm 2.0°$ (c=0.491; chloroform), $R_f=0.35$ (methylene chloride:ethanol=95:5), $R_f=0.63$ (acetone), $R_f=0.73$ (methylene chloride:methanol=9:1).

EXAMPLE 7

From fractions 26-36 of the flash chromatography of Example 5 there is obtained as a secondary product which is unstable in solution N-[2-(tetrahydropyran-4-yl-oxy)-acetyl]-7-hydroxy-staurosporin (mixture of diastereoisomers) in the form of beige crystals of m.p. 235°-237° (sintering from 227°; from ethyl acetate/hexane 1:1) which still contain 0.69 mol of water, $[\alpha]_D^{20} = +209.6 \pm 2.0°$ (c=0.125; chloroform), $R_f=0.24$ (methylene chloride:ethanol=95:5), $R_f=0.55$ (acetone), $R_f=0.55$ (methylene chloride:methanol=9:1).

EXAMPLE 8

Analogously to Example 3 there is obtained from 1.327 g (7.05 mmol) of 2-methyl-2-(tetrahydropyran-4-yloxy)-propionic acid, 1.376 g (9.16 mmol) of 1-hydroxybenzotriazole, 1.757 g (9.16 mmol) of N-ethyl-N'-(3-dimethylaminopropyl)-carbodiimide hydrochloride (EDC) and 2.63 g (5.64 mmol) of staurosporin in 50 ml of absolute N,N'-dimethylformamide, after a reaction time of 24 hours at room temperature under argon, flash chromatography at 0.4 bar (20 ml fractions) on 500 g of silica gel (type Si60, Merck 385, 0.040-0.063 mm) in methylene chloride/acetone (9:1; fractions 1-100) and methylene chloride/acetone (1:1; fractions 100-200), N-[2-methyl-2-(tetrahydropyran-4-yloxy)-propionyl]-staurosporin. For further purification, fractions 134-170 are combined and concentrated to dryness by evaporation under a high vacuum at 30°. The resulting residue is purified again by flash chromatography at 0.4 bar on 100 g of silica gel (type Si60, Merck 9385, 0.040-0.063 mm) in methylene chloride/methanol (98:2; 25 ml fractions). Fractions 21-28 are combined and concentrated by evaporation under a high vacuum at 30°. Recrystallisation of the residue from 13 ml of ethyl acetate/cyclohexane (1:4) gives N-[2-methyl-2-(tetrahydropyran-4-yloxy)-propionyl]-staurosporin in the form of slightly beige crystals of m.p. 209°-211° (sintering from 204°) which still contain 0.38 mol (1.07%) of water; $[\alpha]_D^{20} = +154.7 \pm 2.0°$ (c=0.497; chloroform).

The starting material is obtained as follows:
Stage 8.1a

A solution of 3.48 g (20 mmol) of O-(tetrahydropyran-4-yl)-D-lactic acid in 20 ml of absolute tetrahydrofuran is added dropwise under argon over a period of 15 minutes at 0°-9° to a solution of 20 ml (40 mmol) of lithium diisopropylamide (2-molar solution in tetrahydrofuran/cyclohexane) in 20 ml of absolute tetrahydrofuran. The resulting red solution is then stirred for one hour at 0° and subsequently cooled to −75°. A solution of 2.84 g (1.25 ml, d=2.280; 20 mmol) of methyl iodide in 10 ml of absolute tetrahydrofuran is then added dropwise over a period of 2 minutes, during which time the temperature rises to −61° and the colour of the solution changes to yellow. The yellow solution is stirred for a further 14 hours with gradual warming to room temperature and then the resulting yellow suspension is poured onto 100 ml of ice-water and the batch is extracted twice with 100 ml of ethyl acetate each time. The ethyl acetate phases are then washed once with 50 ml of water. The aqueous phases are combined, acidified with 4N hydrochloric acid and extracted twice with 100 ml of ethyl acetate each time. The ethyl acetate phases are then washed twice with 50 ml of water each time, combined, dried over sodium sulfate and concentrated to dryness by evaporation under a high vacuum at 30°. The crude product is dissolved in 30 ml of ethyl acetate, and 2.73 ml of dicyclohexylamine (Fluka, puriss.) are added to the resulting solution at room temperature. The slowly precipitated crystals are filtered off with suction, washed with a small amount of ethyl acetate and recrystallised a further twice from 30 ml of ethyl acetate each time to give the dicyclohexylammonium salt of 2-methyl-2-(tetrahydropyrano4-yloxy)-propionic acid in the form of colourless crystals which melt at from 131.7° to 137.8° (sintering from 128°).

The salt can be used directly for further synthesis or can be reacted as follows to form the free 2-methyl-2-(tetrahydropyran-4-yloxy)-propionic acid. 3.8 g (0.01 mol) of the dicyclohexylammonium salt are dissolved in 50 ml of water. The solution is adjusted to a pH of 1 with 4N hydrochloric acid. The precipitated dicyclohexylammonium chloride is filtered off with suction and washed with a small amount of water. The aqueous phase is then extracted twice with 100 ml of ethyl acetate each time. The extracts are washed twice with 50 ml of water each time, combined, dried over sodium sulfate and concentrated to dryness by evaporation under a high vacuum at 30°. The residue is recrystallised from cyclohexane to give 2-methyl-2-(tetrahydropyran-4-yloxy)-propionic acid in the form of colourless crystals which melt at from 90.2° to 93.8° (sintering from 79.5°).

Alternatively, 2-methyl-2-(tetrahydropyran-4-yloxy)-propionic acid can be obtained in accordance with a process described by H. Gilman and G. R. Wilder in J. Am. Chem Soc. 77, 6644 (1955) in the following manner:

Stage 8.1b:

5.10 g (50 mmol) of tetrahydro-2H-pyran-4-ol (Fluka, pract.) are dissolved in 48.0 g (60 ml, d=0.79; 826 mmol) of absolute acetone (Fluka, puriss.). 8.11 g (5.45 ml, d=1.49; 68 mmol) of chloroform (Fluka, puriss.) and 9.60 g (240 mmol) of sodium hydroxide (Merck, p.a.) are gradually added to the solution at room temperature, with stirring, the temperature of the reaction mixture rising from 23° to 58° (reflux) over a period of 10 minutes. After 30 minutes at 58° the resulting colourless suspension slowly cools again spontaneously. It is heated to reflux again and stirred for a further 5 hours at that temperature. After cooling again, the batch is concentrated to dryness by evaporation under a high vacuum at 30°. The residue is taken up in 50 ml of water, acidified with 4N hydrochloric acid (pH 1) and extracted twice with 100 ml of ethyl acetate each time. The extracts are washed twice with 50 ml of saturated sodium chloride solution each time. The ethyl acetate phases are combined, dried over sodium sulfate, filtered and concentrated by evaporation again. The residue is purified by column chromatography on 500 g of silica gel (type Si60, Merck 9385, 0.040–0.063 mm) in methylene chloride/methanol/water 70:30:5 (20 ml fractions). Fractions 47–80 are combined and concentrated by evaporation under a high vacuum at 30°. The residue (3.10 g; greasy crystals) is suspended in 30 ml of diethyl ether. The suspension is stirred for ½ hour at room temperature. The resulting crystals are then filtered off with suction and washed with ether. The filter material is taken up in a mixture of 15 ml of water and 20 ml of ethyl acetate, the pH is adjusted to 1 with 4N hydrochloric acid and the ethyl acetate phase is separated off. After washing the ethyl acetate phase with a total of 20 ml of water, all the ethyl acetate phases are combined, dried over sodium sulfate, filtered and concentrated by evaporation under a high vacuum at 30°. The residue (0.41 g) is dissolved in 10 ml of ethyl acetate, and 0.437 ml of dicyclohexylamine (Fluka, puriss.) is added to the solution to give the dicyclohexylammonium salt of 2-methyl-2-(tetrahydropyran-4-yloxy)-propionic acid in the form of colourless crystals which melt at from 136.6° to 138.8° (sintering from 130°) and can likewise be reacted as described above to form the free 2-methyl-2-(tetrahydropyran-4-yl-oxy)-propionic acid.

Alternatively, the dicyclohexylammonium salt of 2-methyl-2-(tetrahydropyran-4-yloxy)propionic acid can also be obtained in accordance with the following process:

Stage 8.1c 10.21 g (100 mmol) of tetrahydro-2H-pyran-4-ol (Fluka, pract.) are dissolved in 350 ml of absolute 1,4-dioxane (Fluka, puriss.). The resulting solution is heated to 65°. Then 12.0 g (300 mmol) of sodium hydride (60% strength, in oil; Fluka, pract.) are added at 65°. The resulting grey suspension is stirred for 3 hours under reflux and subsequently cooled to 65° again, after which a solution of 16.70 g (100 mmol) of α-bromoisobutyric acid (Fluka, pract.) in 150 ml of absolute dioxane is added dropwise over a period of 25 minutes. The resulting suspension is stirred for a further 3 hours under reflux and then for 17 hours at room temperature. 25 ml of water are then carefully added dropwise and the yellow suspension is concentrated to dryness by evaporation under a high vacuum. The residue is taken up in 50 ml of water and extracted twice with 100 ml of ethyl acetate each time. The extracts are then washed once with 50 ml of water. The aqueous phases are combined, adjusted to pH 1 with 4N hydrochloric acid, saturated with sodium chloride and extracted twice with 50 ml of ethyl acetate each time. The extracts are then washed twice with 50 ml of saturated sodium chloride solution each time. All the ethyl acetate phases are combined, dried over sodium sulfate, filtered and concentrated by evaporation under a high vacuum. The residue (5.22 g, yellow oil) is purified by flash chromatography (all 25 ml fractions) at 0.4 bar on 500 g of silica gel (type Si60, Merck 9385; 0.040–0.063 mm) in methylene chloride/methanol (9:1; fractions 1–50), methylene chloride/methanol (4:1; fractions 51–150) and methylene chloride/methanol (7:3; fractions 15 1–225). Fractions 16–200 are combined and concentrated by evaporation under a high vacuum. The residue is stirred with 25 ml of diethyl ether for ¼ hour at room temperature. The resulting crystals are filtered off with suction and washed with diethyl ether. The colourless crystals are then taken up in 10 ml of water, adjusted to pH 1 with 4N hydrochloric acid and extracted twice with 20 ml of ethyl acetate each time. The ethyl acetate phases are washed twice with 10 ml of water each time and then combined, dried over sodium sulfate, filtered and concentrated by evaporation under a high vacuum. The residue is dissolved in 10 ml of ethyl acetate, and 0.317 ml of dicyclohexylamine is added to give the dicyclohexylammonium salt of 2-methyl-2-(tetrahydropyran-4-yloxy)-propionic acid in the form of colourless crystals which melt at from 136.5° to 138.8° (sintering from 130°).

EXAMPLE 9

Tablets each comprising 20 mg of active ingredient, for example one of the compounds of formula I described in the preceding Examples, are prepared in customary manner with the following composition:

| Composition | |
|---|---|
| active ingredient | 20 mg |
| wheat starch | 60 mg |
| lactose | 50 mg |
| colloidal silica | 5 mg |
| talc | 9 mg |
| magnesium stearate | 1 mg |
| | 145 mg |

Preparation

The active ingredient is mixed with a portion of the wheat starch, with the lactose and the colloidal silica and the mixture is forced through a sieve. A further portion of the wheat starch is made into a paste with 5 times the amount of water on a water bath and the powder mixture is kneaded with the paste until a slightly plastic mass has been formed.

The plastic mass is pressed through a sieve having a mesh size of approximately 3 mm and dried, and the resulting dry granules are forced through a sieve again. The remaining wheat starch, the talc and the magnesium stearate are then admixed and the mixture is compressed to form tablets each weighing 145 mg and having a breaking notch.

EXAMPLE 10

Anti-tumour activity of N-[0-(tetrahydropyran-4-yl)-D-lactoyl]-staurosporin in vivo:

The substance is formulated as follows:

12.5 mg of active ingredient are dissolved in 0.25 ml of dimethyl sulfoxide and mixed with 50 µl of Tween 80. 4.7 ml of a 0.9% sodium chloride solution are then added and the whole is mixed thoroughly.

Female Balb/c hairless mice with s.c. transplanted human bladder tumours T24 are used to determine the anti-tumour activity. With the animals under peroral forene narcosis, approximately 25 mg of a solid tumour are placed under the skin on the animals' left flank on day 0 and the small incised wound is closed by means of suture clips. On day 6 after the transplantation, the mice are divided at random into groups of 6 animals and treatment commences. The treatment is carried out for 15 days with the administration once daily of the various doses. The tumours are measured twice a week with a slide gauge and the volume of the tumours is calculated. The results are compiled in the following Table in which "dose" is the daily dose, "admin." is the mode of administration, "exper." is experiment and "T/C %" is the percentage quotient of the values in the treated mice and the untreated control mice. The smaller the quotient, the more effective is the dose administered.

| dose [mg/kg] | admin. | average tumour volume [T/C %] | |
|---|---|---|---|
| | | Exper. 1 | Exper. 2 |
| 6.25 | p.o. | 15 | 12 |
| 3.13 | p.o. | 17 | 14 |
| 1.56 | p.o. | | 31 |
| 0.78 | p.o. | | 58 |
| 3.00 | i.p. | 9 | 11 |
| 1.50 | i.p. | 14 | 19 |
| 0.75 | i.p. | | 32 |
| 0.38 | i.p. | | 62 |
| 0.19 | i.p. | | 74 |

EXAMPLE 11

Determination of the maximum tolerated dose (MTD) of N-[0-(tetrahydropryan-4-yl )-D-lactoyl]-staurosporin 3 female Balb/c mice per dose are treated i.p. or p.o. with N-[0-(tetrahydropyran-4-yl)-D-lactoyl]-staurosporin in dimethyl sulfoxide/Tween 80/sodium chloride solution (see Example 10 for formulation). The dose is increased until animals succumb within 7 days.

MTD (p.o.): 62.5 mg/kg
MTD (i.p.): 31.25 mg/kg

What is claimed is:

1. A tetrahydropyran-4-yloxy-alkanoic acid of formula III

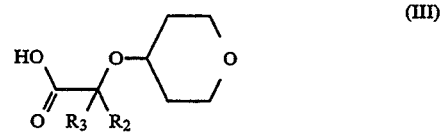

(III)

wherein $R_2$ is $C_{1-4}$alkyl and $R_3$ is hydrogen or $C_{1-4}$alkyl or a salt thereof.

2. The compound of claim 1 which is O-(tetrahydropyran-4-yl)-D-lactic acid or a salt thereof.

3. The compound of claim 1 which is O-(tetrahydropyran-4-yl)-L-lactic acid or a salt thereof.

4. The compound of claim 1 which is 2-methyl-2-(terahydropyran-4yloxy)-propionic acid or a salt thereof.

* * * * *